United States Patent
Yamoto

(10) Patent No.: US 8,961,456 B2
(45) Date of Patent: Feb. 24, 2015

(54) FISTULA CATHETER

(71) Applicant: Covidien LP, Mansfield, MA (US)

(72) Inventor: Natsuko Yamoto, Fukuroi (JP)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/352,081

(22) PCT Filed: Oct. 19, 2012

(86) PCT No.: PCT/US2012/060970
§ 371 (c)(1),
(2) Date: Apr. 16, 2014

(87) PCT Pub. No.: WO2013/059558
PCT Pub. Date: Apr. 25, 2013

(65) Prior Publication Data
US 2014/0236081 A1   Aug. 21, 2014

(30) Foreign Application Priority Data
Oct. 20, 2011   (JP) .................................. 2011-231015

(51) Int. Cl.
*A61M 29/00* (2006.01)
*A61J 15/00* (2006.01)
(Continued)

(52) U.S. Cl.
CPC .......... *A61J 15/0065* (2013.01); *A61J 15/0042* (2013.01); *A61M 25/02* (2013.01);
(Continued)

(58) Field of Classification Search
CPC .................. A61M 25/1018; A61M 25/10181; A61M 25/02; A61M 2025/0233; A61J 15/0065; A61J 15/0042

USPC ........................................ 604/101.01–101.03
See application file for complete search history.

(56) References Cited

U.S. PATENT DOCUMENTS

| | | |
|---|---|---|
| 3,915,171 A | 10/1975 | Shermeta |
| 6,878,130 B2 | 4/2005 | Fourinie et al. |
| 2008/0011973 A1 | 1/2008 | Zamalis |
| 2008/0077043 A1 | 3/2008 | Malbrain et al. |
| 2010/0022969 A1 | 1/2010 | Renaux |

FOREIGN PATENT DOCUMENTS

| | | |
|---|---|---|
| EP | 0853937 A1 | 7/1998 |
| EP | 2065005 A1 | 6/2009 |
| WO | 2008051452 A2 | 5/2008 |

OTHER PUBLICATIONS

Written Opinion of the International Searching Authority dated Mar. 28, 2013 for corresponding PCT Application No. PCT/US2012/060970.
(Continued)

*Primary Examiner* — Nicholas Lucchesi
*Assistant Examiner* — Melissa A Synder

(57) ABSTRACT

A fistula catheter that can prevent separating from the fistula by an inner balloon even if an outer balloon collapses by configuring an internal fixed part with an inner side balloon and an outer side balloon is disclosed. The fistula catheter A has an external fixed part, a supply tube with a primary cavity and a secondary cavity, and an internal fixed part on the tip end side outer periphery of the supply tube, expandable by a compound liquid that includes barium sulfate and distilled water supplied though the secondary cavity. The internal fixed part can be an inner balloon and an outer balloon that communicate with the secondary cavity through filler ports on the peripheral surface of the supply tube. A filter on the filler port can enable distilled water in the compound liquid to be filled into the outer balloon from the secondary cavity through the filter, and the compound liquid can be filled into the inner balloon.

6 Claims, 4 Drawing Sheets

(51) Int. Cl.
*A61M 25/02* (2006.01)
*A61M 25/00* (2006.01)

(52) U.S. Cl.
CPC ......... *A61M25/0009* (2013.01); *A61J 15/0015* (2013.01); *A61M 2025/0233* (2013.01); *A61J 15/0092* (2013.01)
USPC .................................................. 604/101.02

(56) References Cited

OTHER PUBLICATIONS

International Preliminary Report on Patentability dated Apr. 22, 2014 for corresponding PCT Application No. PCT/US2012/060970.
International Search Report dated Mar. 28, 2013 for corresponding PCT Application No. PCT/US2012/060970.

FISTULA CATHETER

FIELD

The present invention relates to a fistula catheter used for supplying fluids such as liquid food and nutrients into a patient.

BACKGROUND

Supplying fluids such as liquid food, nutrients, and the like using a fistula catheter on people with a reduced ability to consume food on their own through the mouth due to old age or illness, hereinafter referred to as patient, has been practiced conventionally. This type of fistula catheter is composed of a supply tube that passes through a hole (fistula) for ingestion provided in the body of a patient, an internal fixed part attached to the tip end part of the supply tube that is inserted into the inner side of the intestinal wall, and an external fixed part that is attached to either the base end part or an interim part of the supply tube and is set up on the skin surface side of the body. Within these types of fistula catheters, there are types in which the internal fixed part is composed of a balloon, and the fistula catheter is prevented from separating from the fistula by expanding the balloon by injecting water into the balloon.

At times when water is used with fistula catheters that utilize a balloon, the fistula catheter can come out from the fistula when the water in the balloon naturally seeps out and the balloon gets smaller or when the balloon deteriorates or breaks due to contact with body fluids or items supplied into the viscera. In these cases, it is common for the fistula to close within several hours making it impossible to reinsert the fistula catheter. Therefore, reforming a fistula is required. To prevent this type of incident, an arrangement has been proposed in U.S. Patent Application Publication No. 2008/011973 A1 in which a reinforcing material is embedded within the balloon to make the balloon less likely to deteriorate or break.

SUMMARY

However, there is a problem with the conventional fistula catheter described above in that it is difficult to manufacture because the reinforcing material is embedded within a membrane-like balloon. Further, strengthening the main body part of the balloon can provide improvement, but strengthening the part that connects the balloon and the supply tube cannot be improved. Therefore, the problem described above occurs when water is released from this type of area due to deterioration.

The present invention advantageously provides a fistula catheter that can prevent coming out from the fistula by an inner balloon even if an outer balloon collapses by configuring the internal fixed part with an inner balloon and an outer balloon. To facilitate understanding of the present invention, descriptions will be provided for each of the compositional elements of the present invention given below with reference numerals for the corresponding location in the embodiment. However, the compositional elements of the present invention should not be interpreted to be limited to the configuration of the corresponding locations illustrated by the reference numerals of the present embodiment.

The characteristics of the configuration of the fistula catheter that pertain to one or more aspects of the present invention can involve a fistula catheter A with an external fixed part 10 arranged on the surface side of the abdominal wall on a fistula 38 formed in the abdominal wall 36 and the intestinal wall 37 of a patient, a supply tube 20 made from a tubular body arranged so that the tip end side connected to the external fixed part extends across from the fistula into the viscera where a primary cavity 21 is formed therein and a secondary cavity 22 is formed in the peripheral wall, and an inner fixed part 30 is provided on the tip end side of the outer periphery of the supply tube that expands within the viscera by supplying a compound liquid of a granular substance B and a liquid W through the secondary cavity; wherein the internal fixed part comprises an inner balloon 31 that communicates with the secondary cavity through filler ports 23 and 24 provided on the peripheral surface of the supply tube, and an outer balloon 32 provided on the outer peripheral side of the inner balloon, respectively, and is configured so that an empty space is formed between the inner balloon and the outer balloon at the time of expansion, and provides a filter 25 on the filler port 24 that communicates with the secondary cavity and the outer balloon so that the liquid within the compound liquid can pass through but the granular substance cannot and can fill the inner balloon with the compound liquid through the filler port 23 that communicates with the inner balloon from the secondary cavity and which can fill the outer balloon with the liquid from within the compound liquid through the filter and the filler port that communicates with the outer balloon from the secondary cavity.

With the fistula catheter according to one or more aspects of the present invention, the internal fixed part can comprise dual balloons that include an inner balloon and an outer balloon. Further, the inner balloon and the outer balloon respectively can communicate with the secondary cavity through filler ports provided on the peripheral surface of the supply tube, and a filter can be provided on the filler port that communicates with the secondary cavity and the outer balloon so that liquid in the compound liquid can pass through from the secondary cavity to the outer balloon but the granular substance cannot pass through. When filling the internal fixed part configured in this manner with compound liquid, the filling into the outer balloon is typically interrupted by the filter, and the compound liquid is preferentially filled into the inner balloon prior to the outer balloon so that the inner balloon is expanded first. Further, when the pressure in the inner balloon and the secondary cavity rises, the liquid in the compound liquid can separate from the granular substance and can pass through the filter to enter into the outer balloon.

As a result, the granular substance can be in the inner balloon and the liquid is filled into the outer balloon, and the inner balloon can expand by being filled with the granular substance while the outer balloon expands by being filled with the liquid separated from the compound liquid by the filter. In addition, because the inner balloon can expand first before the outer balloon when expanding the internal fixed part, the occurrence of the outer balloon expanding first before the inner balloon so the inner balloon regulated by the expansion of the outer balloon not being able to sufficiently expand is alleviated. In this manner, both the inner balloon and the outer balloon can be expanded to a suitable size.

Further, if either the inner balloon filled with the granular substance or the outer balloon filled with liquid were to break, and even if the liquid from the outer balloon were to be released, the other balloon can maintain an expanded state and thereby the fistula catheter can be prevented or inhibited from coming out or being removed from the fistula. If the outer balloon collapses due to a break, the liquid within the outer balloon is released to the outside, but the granular substance within the secondary cavity and the inner balloon is shielded by the filter and is typically not able to enter into the outer balloon, and therefore the inner balloon can maintain an expanded state. Therefore, the fistula catheter can be prevented from coming out from the fistula by the inner balloon. Note, the size at the time of expansion of the inner balloon is preferably set to a size that can prevent the fistula catheter from coming out from the fistula.

Further, if the inner balloon were to break, the granular substance filled within the inner balloon continues to be held within the outer balloon and therefore substantially or virtually no change typically occurs in the expanded state of the outer balloon. In addition, because the granular substance is contained in the compound liquid filled in the internal fixed part, the amount of liquid is reduced by that amount. Even if the liquid filled in the outer balloon were to be released to the outside naturally, a significant change would not occur in the overall capacity of the internal fixed part, and it is unlikely for an effect such as the catheter coming out from the fistula to occur on account of naturally escaping water. Substances that have no harmful effects to humans are preferably used as the liquid and the granular substance that compose the compound liquid.

A membrane or mesh in which a plurality of micro pores is provided can be used as the filter.

One or a plurality of intermediate balloons can be provided between the inner balloon and the outer balloon. A filter that communicates between the intermediate balloon and the secondary cavity by the filler port can be provided on the filler port that allows liquid and a granular substance of a prescribed size contained in a compound liquid to pass through. Accordingly, the compound liquid can be separated into the granular substance and liquid, and rather than just filling an inner balloon and an outer balloon, the compound liquid can fill the intermediate balloon with liquid and the granular substance made of particles of a prescribed size. In this case, a plurality of types of granular substances may be contained within the compound liquid.

Another characteristic of the configuration of the fistula catheter according to one or more aspects of the present invention are in a configuration of the inner balloon by a material with a small stretching property while configuring the outer balloon with a material having a larger stretching property then the inner balloon. According to one or more aspects of the present invention, the compound liquid can be filled inside the inner balloon, and after the inner balloon can be expanded to a prescribed size; liquid in the compound liquid can pass through the filter due to the increased pressure within the inner balloon and secondary cavity thereby filling within the outer balloon; and the outer balloon can be expanded further outside of the inner balloon. Both the inner balloon and the outer balloon can be expanded to a sufficient size.

Another feature or characteristic of the configuration of the fistula catheter in one or more embodiments of the present invention is that the size of the inner balloon when expanded is such that it is constant. In some embodiments in accordance with some aspects of the present invention, the constant size of the inner balloon when expanded can be made to be a constant size that can prevent the fistula catheter from coming out from the fistula. Even if the outer balloon were to break and the liquid were to be released to the outside, the fistula catheter can be securely prevented from coming out from the fistula. Thus, the internal fixed part can be expanded to a predetermined or sufficient size.

Further, another feature of the configuration of the fistula catheter according to some aspects of the present invention is that the inner balloon and the outer balloon are respectively fixed to the supply tube by adhesive, and the positions on the supply tube for the bonded part of the inner balloon 31a and 31b and the bonded part of the outer balloon 32a and 32b are offset along the direction that the supply tube extends. According to one or more aspects of the present invention, protruding to the outer periphery side of the supply tube can be alleviated by overlapping the bonded part of the inner balloon with the supply tube and the bonded part of the outer balloon with the supply tube. Therefore, increased resistance when inserting the internal fixed part into the fistula with the supply tube can be significantly prevented even when configured with dual balloons made up of an inner balloon and an outer balloon.

Another feature of the configuration of the fistula catheter according to one or more aspects of the present invention is in the configuration of the granular substance with barium sulfate. According to some aspects of the present invention, there is no harm even if it were to enter into the viscera such as the stomach, and a compound liquid that contains the granular substance can be obtained that can maintain a prescribed capacity even after the separation removal of the liquid.

One or more aspects of the invention can thus pertain to a fistula catheter to be disposed in a fistula of a patient, comprising an external fixing part configured to be disposed on an abdominal wall of the fistula, a supply tube with a tubular body configured with a tip end side connected to the external fixed part and with a primary cavity formed therein and a secondary cavity formed in a peripheral wall thereof, and an inner fixed part on the tip end side on an outer periphery of the supply tube that expands with a supply of a compound liquid of a granular substance and a liquid through the secondary cavity, the internal fixed part comprises an inner balloon that communicates with the secondary cavity through filler ports provided on the peripheral surface of the supply tube, and an outer balloon provided on the outer peripheral side of the inner balloon, respectively, and is configured so that an empty space is formed between the inner balloon and the outer balloon at the time of expansion, and a filter on the filler port that communicates with the secondary cavity and the outer balloon that the liquid within the compound liquid can pass through but the granular substance cannot and can fill the inner balloon with the compound liquid through the filler port that communicates with the inner balloon from the secondary cavity and which can fill the outer balloon with the liquid from within the compound liquid through the filter and the filler port that communicates with the outer balloon from the secondary cavity. In some cases, the inner balloon can be composed of a material with a small stretching property and the outer balloon is composed of a material with a larger stretching property than the inner material. In further cases, the size of the inner balloon when expanded can be constant. In still further cases, the inner balloon and the outer balloon are respectively fixed to the supply tube by an adhesive, and the positions along the extending direction on the supply tube for the bonded part of the inner balloon and the bonded part of the outer balloon of the supply tube are offset. In yet further cases, the granular substance is barium sulfate.

Further, one or more aspects of the invention can be directed to a method of fabricating a fistula catheter. The method, in some cases, can comprise providing a fistula catheter to be disposed in a fistula of a patient comprising an external fixing part configured to be disposed on an abdominal wall of the fistula, a supply tube with a tubular body configured with a tip end side connected to the external fixed part and with a primary cavity formed therein and a secondary cavity formed in a peripheral wall thereof, and an inner fixed part on the tip end side on an outer periphery of the supply tube that expands with a supply of a compound liquid of a granular substance and a liquid through the secondary cavity, the internal fixed part comprises an inner balloon that communicates with the secondary cavity through filler ports provided on the peripheral surface of the supply tube, and an outer balloon provided on the outer peripheral side of the inner balloon, respectively, and is configured so that an empty space is formed between the inner balloon and the outer balloon at the time of expansion, and a filter on the filler port that communicates with the secondary cavity and the outer balloon that the liquid within the compound liquid can pass through but the granular substance cannot and can fill the inner balloon with the compound liquid through the filler port that communicates with the inner balloon from the secondary cavity and which can fill the outer balloon with the liquid from within the compound liquid through the filter and the filler port that communicates with the outer balloon from the secondary cavity.

DETAILED DESCRIPTION

Figure 1:
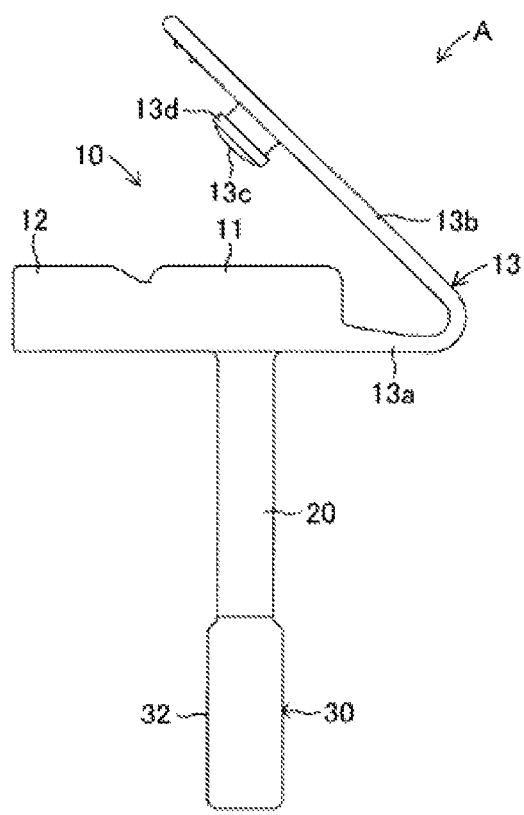
FIG. 1 is a side view illustrating the fistula catheter that relates to an embodiment of the present invention.
Figure 2:
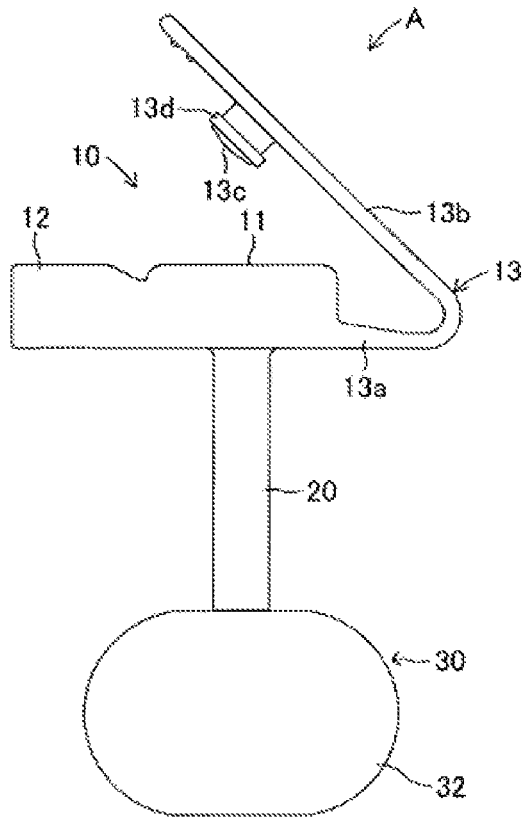
FIG. 2 is a side view illustrating a state in which the internal fixed part of the fistula catheter exemplarily illustrated in FIG. 1 is expanded.

A detailed description is provided with reference to the drawings of an embodiment of the fistula catheter that relates to the present invention. FIG. 1 and FIG. 2 exemplarily illustrate fistula catheter A that relates to the same embodiment. Fistula catheter A can comprise an external fixed part 10, a supply tube 20 that is connected to the bottom side of the external fixed part 10, and an internal fixed part 30 that is attached to the bottom part of the supply tube 20. Preferably, the external fixed part 10 is made of a polyurethane and silicon rubber, and the supply tube 20 is made of silicon rubber, and the internal fixed part 30 is made of polyurethane and silicon rubber. In the following description, terms for the front and rear direction, left and right direction, and up and down direction, will be listed based on FIG. 1 and FIG. 2.

Figures 3, 4:
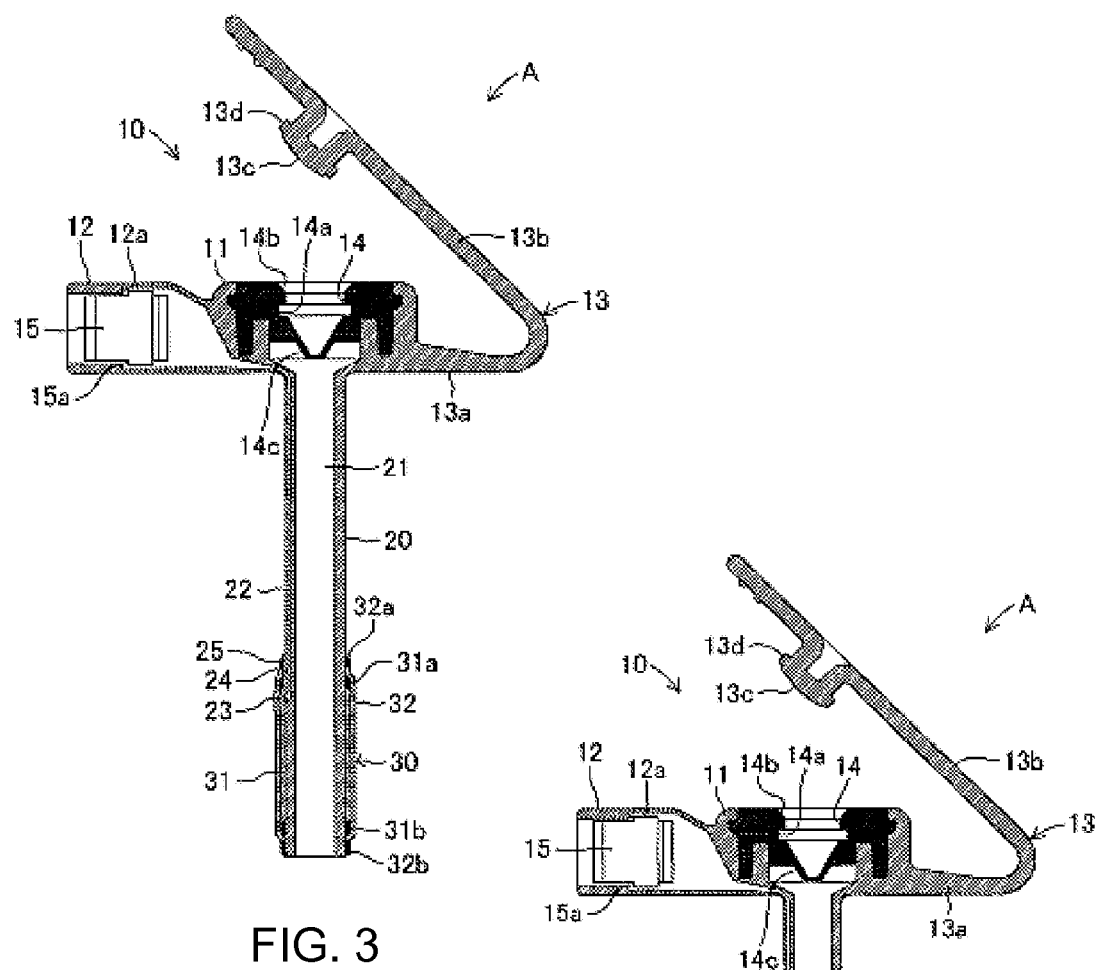
FIG. 3 is a cross sectional view of the fistula catheter exemplarily illustrated in FIG. 1.
FIG. 4 is a cross sectional view illustrating the fistula catheter exemplarily illustrated in FIG. 2.

The external fixed part 10, as exemplarily illustrated in FIG. 3 and FIG. 4, comprises a retention part main body 11 configured in a slightly thicker ring shape, a side port 12 that is projected in the left horizontal direction from the left side part of the retention part main body 11, and a long and thin lid part 13 that is projected in the right direction from the bottom part of the right side part of the retention part main body 11. Further, an opening part 14 that vertically penetrates is formed in the center of the retention part main body 11, and an engaging groove part 14a is formed along the circular perimeter in the center of the vertical direction on the inner peripheral surface of the opening part 14. Further, the top part of the opening part 14 is configured with a slanted part 14b in which the diameter is larger when moving from the top part to the bottom part, and a one-way valve 14c that projects downward is formed on the bottom part of the opening part 14. The one-way valve 14c is configured by a valve that provides a slit (not illustrated) so that fluids such as liquid foods, nutrients, medicines, and moisture and the like, can pass through from the top to the bottom in the retention part main body 11 but are prevented from flowing in reverse.

The side port 12 is configured in a cylindrical shape and the top of the side portion of the retention part main body 11 thereof is configured by a slanted part in which the right side extends downward. Further, the diameter of the inner peripheral surface of the side port 12 is slightly larger on the right side portion then on the left side portion and a step 12a is formed at the boundary thereof. In addition, an injection valve 15 is arranged within the side port 12 with the ability to travel laterally. The injection valve 15 is configured by a cylindrically shaped valve body with a step difference in which the right side portion has a larger diameter than the left side portion, and a step 15a is formed at the boundary thereof.

In addition, a small diameter portion is positioned on the left side within the side port 12, and a large diameter portion is positioned on the right side within the side port 12, and the injection valve 15 is arranged with the ability to travel within the side port 12. Further, the side port 12 is closed when the injection valve 15 is positioned to the left so that the step 15a contacts against the step 12a of the inner peripheral surface of the side port 12, and when it is moved to the right side from that state, the side port 12 is opened by the formation of a gap with the inner peripheral surface of the side port 12. Further, although omitted from the drawings, a spring member is arranged between the insertion valve 15 and the side of the retention part main body 11 within the side port 12, and the insertion valve 15 is biased to the left side by this spring member to close the side port 12.

The lid 13 is configured of a connecting piece 13a that extends from the right side of the retention part main body 11 toward the right horizontal direction, a belt like connecting part 13b connected to the tip end of the connecting piece 13a, and a plug part 13c provided on the tip end side of the belt like connecting part 13b. The connecting piece 13a is configured by a plate like portion that is unlikely to deform in which the belt like connecting part 13b connects to the retention part main body 11 and has a function to prevent the fistula catheter A within the viscera from being pulled. The belt like connecting part 13b has flexibility and is bent so as to pivot upward and downward centrally around the connecting part with the connecting piece 13a, and can bend at a sharp angle. In addition, the plug part 13c is provided at the tip end side portion of the belt like connecting part 13b.

The plug part 13c is provided on the belt like connecting part 13b such that it opposes the opening part 14 when the tip end side portion is positioned on the upper surface of the retention part main body 11 by bending the belt like connecting part 13b. The plug part 13c is configured with a cupped cylindrical protrusion with a short length that can fit into the opening part 14, and a protruding part 13d along the circular perimeter is provided on the outer circumference surface thereof that can engage with the ability to attach to and detach from a groove part 14a on the opening part 14. Therefore, the protruding part 13d can engage with the groove part 14a by the plug part 13c being pressed into the opening part 14 by bending the belt like connecting part 13b, and by so doing, the opening part 14 of the retention part main body 11 can be closed. Further, the opening part 14 of the retention part main body 11 can be opened by removing the engagement between the opening part 14 and the plug part 13c by pulling the tip end side portion of the belt like connecting part 13b.

The supply tube 20 is configured of a tube shaped member that has a primary cavity 21 formed therein to supply fluids such as liquid food, nutrients, liquid medicines, and moisture and the like into the stomach of the patient, and has a secondary cavity 22 formed on the wall part supply the compound liquid made of, for example, barium sulfate B and distilled water W, to the internal fixed part 30. The top end of the primary cavity 21 communicates with the opening part 14 through the one-way valve 14c of the external fixed part 10, and the bottom end of the primary cavity 21 opens at the bottom end of the supply tube to communicate with to the outside. Further, the top end of the secondary cavity 22 communicates with the right side lower part within the end port 12, and the bottom end of the secondary cavity 22 bends and opens toward the outer peripheral surface slightly more to the lower part side portion than the center in the vertical direction on the outer peripheral surface of the supply tube 20. The filler port 23 is configured by this opening.

Figure 5:
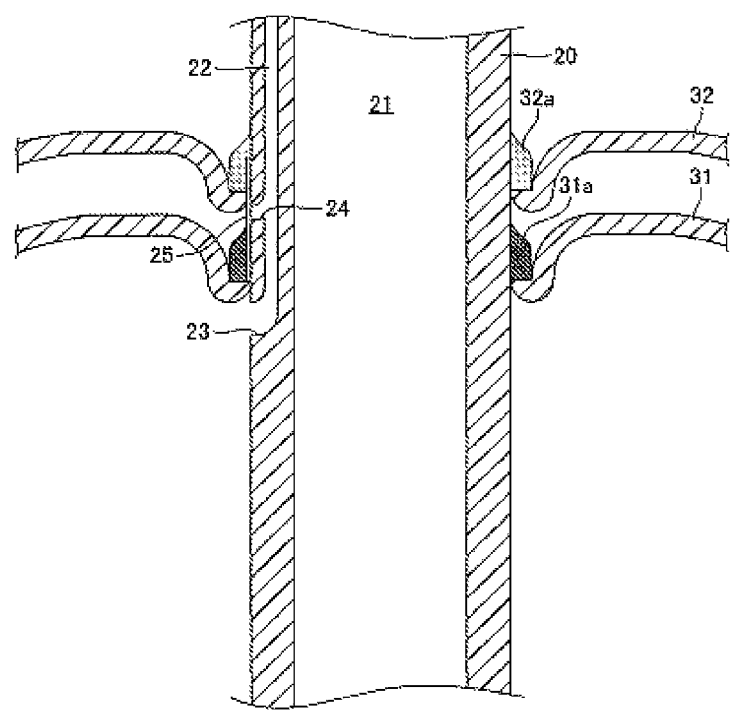
FIG. 5 is an enlarged cross sectional view of the bonded part of the upper part of the internal fixed part and the supply tube.

Further, as exemplarily illustrated in FIG. 5, the filler port 24 which communicates to the outside is formed by being bent to face the outer peripheral surface slightly more to the top than the filler port 23 of the bottom end of the secondary cavity 22. The diameter of the filler port 23 is set up to be longer than the diameter of the filler port 24. Further, the filter 25 is provided on the filler port 24. The size of the holes for the filter 25 is determined according to the size of the granules for the granular substance, and the filter is formed of a membrane or a mesh in which micro pores having a size in a range of, for example, between 0.1 to 1 μm are formed throughout its entirety, and which allows distilled water W to pass from within the secondary cavity 22 to the outside but prevents the barium sulfate B from passing through. Preferably, the filter 25 is formed from a fluororesin or a polyethersulfone.

The internal fixed part 30 is provided on the outer peripheral surface of the supply tube 20 between the bottom end part of the supply tube 20 and the part slightly higher than the part in which the filler port 24 is provided. The internal fixed part 30 is made of the inner balloon 31 and the outer balloon 32, and the inner balloon 31 is preferably polyurethane, and the outer balloon 32 is preferably silicon rubber. Moreover, polyurethane and silicon rubber are preferably selected as the materials of the internal fixed part 30 because they have excellent properties for formability, drug resistance, and biocompatibility and are provided with properties with little comparative likelihood for water release (gas release). The inner balloon 31 is provided between the portion between the portion where the filler port 23 is provided and the portion where the filler port 24 is provided on the outer peripheral surface of the supply tube 20 and the portion slightly above the lower end part of the supply tube 20, and is configured to provide little stretching property in a substantially pouch like body with a hole part formed vertically.

The inner balloon 31 covers the outer peripheral surface of the supply tube 20 and is fixed to the supply tube 20 by gluing the top end part and the bottom and part of the inner peripheral surface to the outer peripheral surface of the supply tube 20 by an adhesive and thereby expands by being filled with the compound liquid from the secondary cavity 22 through the filler port 23. Moreover, FIG. 4 exemplarily illustrates a state in which the liquid in the compound liquid is filled into the outer balloon 32, and in this state, the inner balloon 31 is filled mostly with barium sulfate B. At this time, the inner balloon 31 expands to a nearly spherical shape with the lateral direction and front and back direction longer than the vertical direction, and the bonded parts 31a and 31b with the supply tube 20 on the inner balloon 31 are buried by the top part and bottom part of the expanded inner balloon 31. Further, the inner balloon 31 may be expanded to a constant size, for example, a constant size in order to maintain the fistula catheter A in place in the fistula 38 (see the exemplary embodiments presented at FIG. 6 and FIG. 7).

The outer balloon 32 is provided on the outer peripheral surface of the supply tube 20 between the bottom end part of the supply tube 20 and the part slightly higher than the part in which the filler port 24 is provided, and is configured with a cylindrical body that provides a larger stretching property than the inner balloon 31. The outer balloon 32 covers the inner balloon 31 and is fixed to the supply tube 20 by gluing the top end part and the bottom end part of the inner peripheral surface to the outer peripheral surface at portions that are above and below that of the inner balloon 31.

The upper bonded part 32a on the supply tube 24 for the outer balloon 32 is positioned higher than the bonded part 31a of the inner balloon 31, and the lower bonded part 32b on the supply tube 20 for the outer balloon 32 is positioned lower than the bonded part 31b of the inner balloon 31. Further, when the outer balloon 31 is collapsed prior to expanding, the inner balloon 31 is flattened due to the compression on the outer peripheral surface of the supply tube 20, and, as exemplarily illustrated in FIG. 1 and FIG. 3, the outer balloon 32 maintains a cylindrical shape. Further, the outer balloon 32 is expanded as exemplarily illustrated in FIG. 2 and FIG. 4 by being filled with distilled water W that has been separated from the compound liquid through the filter 25 and through the filler port 24 from the secondary cavity 22. At this time, the outer balloon 32 expands to a nearly spherical shape with the lateral direction and front and back direction longer than the vertical direction, and the bonded parts 32a and 32b of the outer balloon 32 are buried by the top part and bottom part of the expanded outer balloon 32.

Figure 6:
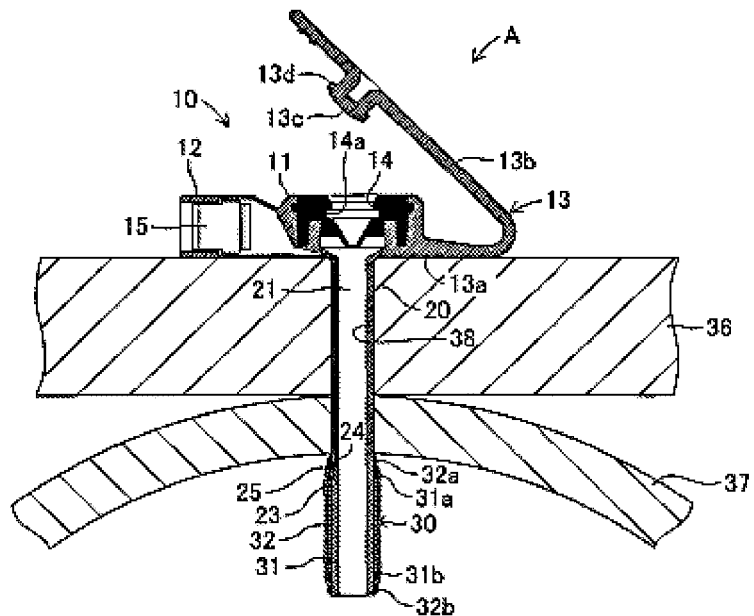
FIG. 6 is a cross sectional view illustrating a state in which the fistula catheter is inserted into a fistula.
Figure 7:
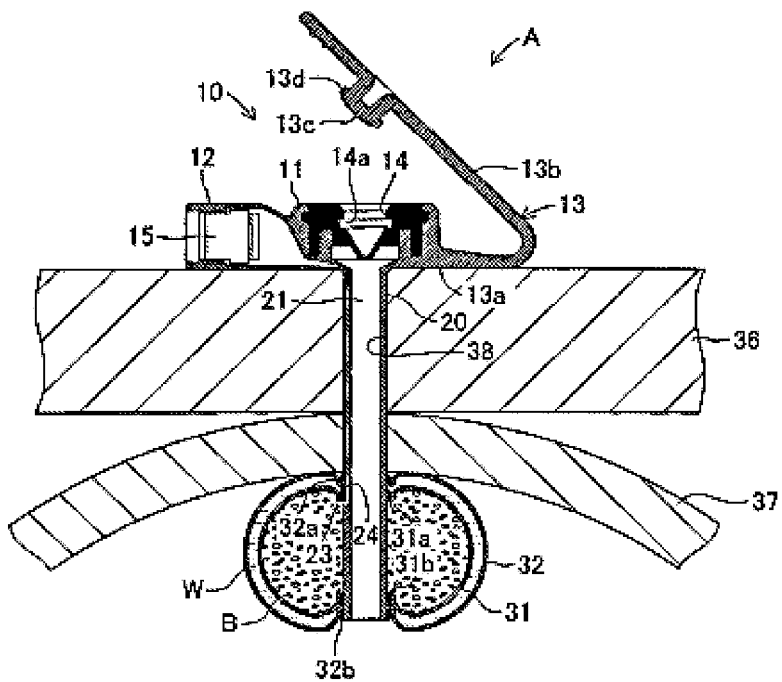
FIG. 7 is a cross sectional view illustrating a state in which the internal fixed part of the fistula catheter exemplarily illustrated in FIG. 6 is expanded.

With this configuration, when the fistula catheter A is used, the fistula catheter A is first passed through the fistula 38 formed in the abdomen while 36 and the stomach wall 37 of the patient as exemplarily illustrated in FIG. 6, in a state in which the interior fixed part 30 is in a collapsed state. In this case, the outer balloon 32 takes a cylindrical shape flattening the inner balloon 31, and the bonded parts 32a and 32b of the outer balloon are in a different position on the outer peripheral surface of the supply tube 20 in the bonded parts 31a and 31b. The internal fixed part 30 can be in a sealed state to the outer peripheral surface of the supply tube 20 without being overall bulky. The supply tube 20 and the internal fixed part 30 can smoothly pass into the fistula 38.

Further, when the internal fixed part 30 enters the inside of the stomach wall 37, the filler port of the injecting device (not shown) for injecting the compound liquid is inserted into the side port 12 and the compound liquid is injected from the injecting device into the inner balloon 31 and the outer balloon 32 through the secondary cavity 22. At this time, the injection valve 15 moves to the retention part main body 11 side by resistance on the spring member compressed in the filler port of the injection device, and the compound liquid supplied from the injection device passes through the gap between the side port 12 and the injection valve 15 to enter into the secondary cavity 22. Further, the compound liquid passes through the filler port 23 to enter into the inner balloon 31. In addition, a portion of the distilled water W in the compound liquid passes through the filter 25 to enter into the outer balloon 32.

When the compound liquid and the distilled water W are filled into the inner balloon 31 and the outer balloon 32, the majority of the compound liquid supplied to the secondary cavity 22 from the injection device is supplied into the inner balloon 31 from the filler port 23, and the inner balloon 31 is expanded to a prescribed size. In addition, the pressure within the inner balloon 31 rises and as the pressure within the secondary cavity 22 rises, the distilled water W in the compound liquid is separated from the barium sulfate B and passes through the filler port 24 and the filter 25 and is supplied into the outer balloon 32. Therefore, the inner balloon 31 is expanded by the filled state of the barium sulfite B, and the outer balloon 32 expands by the filled state of the distilled water W.

By so doing, the inner balloon 31 can be expanded to a constant size such that the fistula catheter A can be prevented from being taken out from the fistula 38, and further, the outer balloon 32 is expanded by maintaining a gap with the inner balloon 31. As exemplarily illustrated in FIG. 7, the upper surface of the outer balloon 32 contacts the inner surface of the stomach wall 37. As a result, the fistula catheter A is prevented from coming out from the fistula 38 and maintains an attached state with the abdominal part of the patient. In this case, the bonded part 32a of the outer balloon 32 does not contact the stomach wall 37 but only the curved surface portion of the upper part of the outer balloon 32 contacts the stomach wall 37.

When the fistula catheter A is in place in the fistula 38, the injection device is removed from the side port 12. By so doing, the injection valve 15 moves to the open side of the side port 12 due to the elasticity of the spring member and the side port 12 closes. By closing the side port 12 with the injection valve 15, the inner balloon 31 and the outer balloon 32 maintain their expanded states. In this case, even if an external force is applied to the outer balloon 32 due to contact or the like with the external balloon 32 by the stomach wall 37 through peristaltic movement of the stomach, the inner balloon 31 and the outer balloon 32 maintain their expanded states.

Further, when fluids such as liquid food, nutrients, liquid medicines, and moisture in the like are ingested by the patient, the opening part 14 of the external fixed part 10 is in an open state a fluid supply tube (not shown) is connected to the opening part 14. In this state, fluids enter into the fluid supply tube from the end part opening of the fluid supply tube. By so doing, fluids enter into the opening part 14 from the fluid supply tube, and after passing through the one-way valve 14c, are supplied into the stomach of the patient through the primary cavity 21. Further, after supplying the fluids, the fluid supply tube is removed from the external fixed part 10, the opening part 14 of the external fixed part 10 is closed by the plug part 13c of the lid 13. In this manner, fluids supplied into the stomach can be prevented from reverse flow due to the one-way valve 14c and the plug part 13c.

In this manner with the fistula catheter A placed in the fistula 38, the bonded part 32a of the outer balloon 32 does not contact the stomach wall 37 but only the curved surface portion of the top part of the outer balloon 32 contacts the stomach wall 37, and therefore gastric ulcers as well as damage to the stomach wall 37 due to the outer balloon 32 stimulating the stomach wall 37, can be prevented. In cases in which the stomach shrinks due to being empty and the stomach wall 37 contacts the outer balloon 32 on the bottom side of the stomach, the bonded part 32b of the outer balloon 32 does not contact the stomach wall 37 but only the curved surface portion of the bottom part of the outer balloon 32 contacts the stomach wall 37, and therefore gastric ulcers as well as damage to the stomach wall 37 due to the outer balloon 32 stimulating the stomach wall 37, can be prevented.

By doing as described above, the fistula catheter A can be used, and while in use, the outer balloon 32 may deteriorate and break. In such a case, the distilled water W in the outer balloon 32 will be released, however, the inner balloon 31 will maintain an expanded state due to the barium sulfate B, and the fistula catheter A will maintain a usable state without coming out from the fistula 38. Further, because only distilled water W is released from the broken outer balloon 32, there is no harm of it entering the stomach. If the inner balloon 31 breaks or a leak occurs in the inner balloon 31, the barium sulfate B in the inner balloon 31 will be held within the outer balloon 32 as is and will mix with the distilled water W and no particular problem will occur.

In this manner, the fistula catheter A according to the present embodiment is composed of the internal fixed part 30 with an inner balloon 31 and an outer balloon 32. Further, the secondary cavity 22 communicates with the inner balloon 31 through the filler port 23 provided on the peripheral surface of the supply tube 20. In addition, the secondary cavity 22 communicates with the outer balloon 32 through the filler port 24 and the filter 25 provided on the peripheral surface of the supply tube 20, and it is configured so that only distilled water W separated from the compound liquid can be filled within the outer balloon 32. The inner balloon 31 is filled with the compound liquid and the pressure within the inner balloon 31 and the secondary cavity 22 rises, and on account of the pressure rising, the distilled water W inside the compound liquid passes through the filter 21 to fill the outer balloon 32, and thereby, both the inner balloon 31 and the outer balloon 32 can be expanded.

In this case, because the filter 25 is provided with the filler port 24 that communicates with the outer balloon 32, the inner balloon 31 is preferentially filled with the compound liquid prior to the outer balloon 32 being filled with the distilled water W. Because the distilled water W separated from the compound liquid within the inner balloon 31 and the secondary cavity 22 is filled in the outer balloon 32, the occurrence of the outer balloon 32 expanding first so the inner balloon 31 regulated by the expansion of the outer balloon 32 not being able to sufficiently expand is alleviated. Therefore, both the inner balloon 31 and the outer balloon 32 can be expanded to a suitable size. Even if either one of the inner balloon 31 filled with barium sulfite B or the outer balloon 32 filled with distilled water W were to collapse due to a break, the other one can maintain and expanded state, and therefore can prevent the fistula catheter A from coming out from the fistula 38.

Because barium sulfite B is contained in the compound liquid filled in the internal fixed part 30, the amount of distilled water W can be reduced by that amount, and therefore, even if the distilled water W filled in the outer balloon 32 is naturally released to the outside, the internal fixed part 30 can maintain a certain degree of size, and thus the fistula catheter A can be prevented from coming out from the fistula 38. Because the inner balloon 31 is composed of polyurethane having a small stretching property and the outer balloon 32 is composed of silicon rubber having a large stretching property, even after the inner balloon 31 is filled with barium sulfate B and the inner balloon 31 is expanded to a prescribed size, if the compound liquid is further supplied, the distilled water W therein is filled into the outer balloon 32, and the outer balloon 32 is further expanded outside of the inner balloon 31. Therefore, both the inner balloon 31 and the outer balloon 32 can be expanded to a sufficient size.

The size at the time of expansion of the inner balloon 31 is preferably set to be at least a constant size that can prevent the fistula catheter A from coming out from the fistula 38. Even if the outer balloon 32 were to break and the distilled water W therein were to be released to the outside, the fistula catheter A can be security prevented from coming out from the fistula 38. Therefore, the internal fixed part 30 can be expanded to a necessary and sufficient size.

Because the positions of the bonded parts 31a and 31b of the inner balloon 31 with the supply tube 20, and the bonded parts 32a and 32b of the outer balloon 32 with the supply tube 20 are offset, protruding to the outer periphery side of the supply tube can be alleviated by overlapping the bonded parts 31a and 31b with the bonded parts 32a and 32b. Therefore, increased resistance when inserting the internal fixed part 30 into the fistula 38 with the supply tube 20 can be significantly prevented even when configuring with dual balloons that include an inner balloon 31 and an outer balloon 32. Because the granular substance is composed of barium sulfate B and the liquid is composed of distilled water W, there is no harm to humans and even after the distilled water W is removed due to discharge, the compound liquid can be obtained so as to maintain a prescribed capacity. Therefore, no particular problem would likely occur even if the compound liquid were to enter inside the stomach.

The fistula catheter according to some aspects of the present invention is not particularly limited to each embodiment described above but can be appropriately modified for implementation. For example, with the embodiment described above, a compound liquid made of barium sulfite B and distilled water W was used to expand the inner balloon 31 and the outer balloon 32, but other granular substances that can be formed in tiny granules of agar and that are not harmful to humans can be used instead of barium sulfate B, and other liquids that are not harmful to humans can be used instead of distilled water W. Further, the fistula catheter is not restricted to the outside fixed part 10 being connected to the top end of the supply tube 20, but a flange shaped outside fixed part can also be connected to an interim part of a long supply tube. In addition, with the embodiment described above, the viscera were represented by the stomach, but the viscera are not limited to the stomach, but may also be an intestine, bladder, or the like.

With the embodiment described above, the internal fixed part 30 was composed of an inner balloon 31 and outer balloon 32, but one or a plurality of intermediate balloons can also be provided between the inner balloon 31 and the outer balloon 32. In this case, a filter that communicates between the intermediate balloon and the secondary cavity by the filler port is provided on the filler port that allows liquid and a granular substance of a prescribed size contained in a compound liquid to pass through, and the filter may be a membrane or a mesh in which micro pores are formed throughout in the size in a range of approximately, for example, 0.05 to 0.5 μm. The compound liquid is separated into the granular substance and liquid, and rather than just filling the inner balloon 31 and the outer balloon 32, the compound liquid can fill the intermediate balloon with liquid and the granular substance made of particles of a prescribed size. Additionally, a plurality of types of granular substances may be contained within the compound liquid. Further, the materials composing each portion provided in the fistula catheter A can be suitably modified.

What is claimed:

1. A fistula catheter to be disposed in a fistula of a patient, comprising:
    an external fixing part configured to be disposed on an abdominal wall of the fistula,
    a supply tube with a tubular body configured with a tip end side connected to the external fixed part and with a primary cavity formed therein and a secondary cavity formed in a peripheral wall thereof, and
    an inner fixed part on the tip end side on an outer periphery of the supply tube that expands with a supply of a compound liquid of a granular substance and a liquid through the secondary cavity, the internal fixed part comprises an inner balloon that communicates with the secondary cavity through filler ports provided on the peripheral surface of the supply tube, and an outer balloon provided on the outer peripheral side of the inner balloon, respectively, and is configured so that an empty space is formed between the inner balloon and the outer balloon at the time of expansion, and a filter on the filler port that communicates with the secondary cavity and the outer balloon that the liquid within the compound liquid can pass through but the granular substance cannot and can fill the inner balloon with the compound liquid through the filler port that communicates with the inner balloon from the secondary cavity and which can fill the outer balloon with the liquid from within the compound liquid through the filter and the filler port that communicates with the outer balloon from the secondary cavity.

2. The fistula catheter according to claim 1, wherein the inner balloon is composed of a material with a small stretching property and the outer balloon is composed of a material with a larger stretching property than the inner material.

3. The fistula catheter according to claim 1, wherein the size of the inner balloon when expanded is constant.

4. The fistula catheter according to claim 1, wherein the inner balloon and the outer balloon are respectively fixed to the supply tube by an adhesive, and the positions along the extending direction on the supply tube for the bonded part of the inner balloon and the bonded part of the outer balloon of the supply tube are offset.

5. The fistula catheter according to claim 1, wherein the granular substance is barium sulfate.

6. A method of fabricating a fistula catheter, comprising providing a fistula catheter to be disposed in a fistula of a patient comprising
    an external fixing part configured to be disposed on an abdominal wall of the fistula,
    a supply tube with a tubular body configured with a tip end side connected to the external fixed part and with a primary cavity formed therein and a secondary cavity formed in a peripheral wall thereof, and
    an inner fixed part on the tip end side on an outer periphery of the supply tube that expands with a supply of a compound liquid of a granular substance and a liquid through the secondary cavity, the internal fixed part comprises an inner balloon that communicates with the secondary cavity through filler ports provided on the peripheral surface of the supply tube, and an outer balloon provided on the outer peripheral side of the inner balloon, respectively, and is configured so that an empty space is formed between the inner balloon and the outer balloon at the time of expansion, and a filter on the filler port that communicates with the secondary cavity and the outer balloon that the liquid within the compound liquid can pass through but the granular substance cannot and can fill the inner balloon with the compound liquid through the filler port that communicates with the inner balloon from the secondary cavity and which can fill the outer balloon with the liquid from within the compound liquid through the filter and the filler port that communicates with the outer balloon from the secondary cavity.

* * * * *